(12) United States Patent
Ao

(10) Patent No.: US 9,459,198 B2
(45) Date of Patent: Oct. 4, 2016

(54) PRESSING AND TEARING APPARATUS AND METHOD FOR PEELING RATE TESTS

(71) Applicant: SHENZHEN CHINA STAR OPTOELECTRONICS TECHNOLOGY CO., LTD., Shenzhen, Guangdong (CN)

(72) Inventor: Xueli Ao, Shenzhen (CN)

(73) Assignee: SHENZHEN CHINA STAR OPTOELECTRONICS TECHNOLOGY CO., LTD., Shenzhen (CN)

( * ) Notice: Subject to any disclaimer, the term of this patent is extended or adjusted under 35 U.S.C. 154(b) by 178 days.

(21) Appl. No.: 14/359,574

(22) PCT Filed: Mar. 28, 2014

(86) PCT No.: PCT/CN2014/074288
§ 371 (c)(1),
(2) Date: May 20, 2014

(87) PCT Pub. No.: WO2015/139335
PCT Pub. Date: Sep. 24, 2015

(65) Prior Publication Data
US 2015/0260636 A1 Sep. 17, 2015

(51) Int. Cl.
*G01N 19/04* (2006.01)
(52) U.S. Cl.
CPC ....... *G01N 19/04* (2013.01); *G01N 2203/0091* (2013.01)

(58) Field of Classification Search
CPC .................................. G01N 3/08; G01N 19/04
USPC ............................................................ 73/827
See application file for complete search history.

(56) References Cited

U.S. PATENT DOCUMENTS

| 5,931,070 A * | 8/1999 | Miyajima | ............ B21D 28/002 83/39 |
| 6,584,858 B1 * | 7/2003 | Miyazawa | ............. G01N 19/04 73/150 A |
| 7,628,066 B2 * | 12/2009 | Deng | ....................... G01N 3/24 73/150 A |

* cited by examiner

*Primary Examiner* — Lisa Caputo
*Assistant Examiner* — Octavia Hollington

(57) ABSTRACT

The present application relates to a pressing and tearing apparatus and method for peeling rate tests, wherein the apparatus comprises a working table configured to place a sample; a press mechanism disposed above the working table, and being capable of synchronously rolling and translating relative to the working table; an input unit configured for inputting a preset pressing force value and a preset tearing force value; a pressure sensor and tension sensor; a controller electrically connected to the input unit, the pressure sensor, and the tension sensor respectively; and a drive mechanism configured to drive the working table to move upward or downward and drive the press mechanism to roll and translate synchronously relative to the working table under the control of the controller.

14 Claims, 5 Drawing Sheets

PRESSING AND TEARING APPARATUS AND METHOD FOR PEELING RATE TESTS

TECHNICAL FIELD

The present application relates to the technical field of peeling rate test, and more particularly, relates to a pressing and tearing apparatus and a method for peeling rate tests.

BACKGROUND

In the panel display industry, a color display generally achieves color display by an RGB color filter. However, RGB color resists may be peeled from the display and form bright points, because different parts of each of the RGB color resists may provide different adhesions to adhere to a substrate respectively. The bright points may have great influence on the quality of the display, and thus become a major defect of a screening process using the display. Therefore, the adhesions between the RGB color resists and the substrate become key parameters for the assessment of material.

At present, a widely used method for the assessment of material and the adhesion test for new products is Cross-Cut Test. The process of the Cross-Cut Test generally includes the following operations: drawing crossed meshes on an area to be tested using a cross-cut tester; implementing adhesive tape treatments to the area to be tested, and finally estimating adhesion levels according to an area of a part of a coating layer peeled from a substrate within the crossed mesh region.

However, in this method, the pressing operation for the adhesive tape is greatly influenced by artificial factors. Different testers may apply different pressing forces to the adhesive tapes, and they may also apply different tearing angles and tearing forces to the adhesive tapes when the adhesive tapes are torn off. Even though one tester performs parallel tests on the same sample, he/she cannot ensure that all the forces applied to the sample are the same. Therefore, operation errors of this test method may be large.

In order to avoid the operation errors caused by one or more testers, improve the repeatability of the experiment data, reflect the performance of material more precisely, and assess and select material meeting the requirements so that the quality of the products can be guaranteed, it is necessary to design an apparatus and a method, which can ensure the uniformity of pressing forces, tearing forces, and tearing angles applied to adhesive tapes in the testing processes.

SUMMARY

The objective of the present application is that: to overcome the drawbacks of the conventional testing method and testing apparatus that the pressing forces, tearing forces, and tearing angles applied to the adhesive tapes are non-uniform, which may result in that the samples are tested under different treating conditions and further cause great operation errors, bad repeatability, and poor stability, application a pressing and tearing apparatus and a method for peeling rate tests are provided.

In accordance with one aspect of the present application, a pressing and tearing apparatus for peeling rate tests is provided, which comprises a working table configured to carry a sample;
a working table configured to place a sample;
a press mechanism disposed above the working table, and being capable of synchronously rolling and translating relative to the working table;
an input unit configured for inputting a preset pressing force value and a preset tearing force value;
a pressure sensor configured for detecting a pressing force between the sample and the press mechanism;
a tension sensor configured for detecting a tearing force between the sample and the press mechanism;
a controller electrically connected to the input unit, the pressure sensor, and the tension sensor respectively; wherein, the controller is configured to compare the detected pressing force value received from the pressure sensor or the detected tearing force value received from the tension sensor with the preset pressing force value and the preset tearing force value received from the input unit, and drive the working table to move upward or downward for adjusting the pressing forces or the tearing forces; the controller is further configured to drive the press mechanism to roll and translate synchronously relative to the working table for pressing or tearing off adhesive tapes; and
a drive assembly configured to drive the working table to move upward or downward and drive the press mechanism to roll and translate synchronously relative to the working table under the control of the controller.

In one embodiment, the pressing and tearing apparatus for peeling rate tests includes a base plate and a holding element; the controller and the holding element are fixed on the base plate, and a mounting slot configured for mounting a first fixing member of the press mechanism in is defined in the holding element.

In this embodiment, the press mechanism further includes a second fixing member and a rolling member configured to press and tear off the adhesive tapes; one end of the second fixing member is fixedly connected to the first fixing member, and the rolling member is rotatably mounted on the second fixing member.

In this embodiment, the second fixing member includes a mounting portion configured for rotatably mounting the rolling member to be rotatably;
the mounting portion includes two mounting plates disposed opposite to each other; one end of one of the mounting plates is connected to one end of the other of the mounting plates by a connection plate; a spindle is disposed between surfaces of the two mounting plates that are opposite to each other; the rolling member is disposed between the two mounting plates and is rotatable relative to the spindle.

Yet in this embodiment, the second fixing member further includes a connection portion; one end of the connection portion is fixedly connected to the first fixing member, and the other end of the connection portion is fixedly connected to the connection plate of the mounting portion.

In another embodiment, two ends of the first fixing member project from the mounting slot; and one end of the first fixing member forms a moving part configured to drive the first fixing member to move inside the mounting slot.

In a further embodiment, the drive assembly includes a table drive mechanism, and the table drive mechanism includes a second motor and a screw rod; wherein the second motor is electrically connected to the controller; one end of the screw rod is connected to the second motor by a drive connection, and the other end of the screw rod is connected to the working table by a screw connection.

In this embodiment, a guide slot is defined in the top of the controller;
the table drive mechanism further includes a first motor, a belt drive unit, and a guide block; wherein, the first motor is electrically connected to the controller; the belt drive unit is connected to the first motor by a drive connection; the guide block is disposed on the belt drive unit and is limited in the guide slot; the guide block is movable in the guide slot with the rotation of a convey belt of the belt drive unit; and the second motor is fixed on the guide block.

In a further embodiment, the drive assembly includes a pressing drive mechanism, and the pressing drive mechanism includes a motor electrically connected to the controller and a drive element configured to drive the press mechanism to roll and translate synchronously relative to the working table.

In a further embodiment, the first fixing member of the press mechanism is movable in the mounting slot of the holding element.

In accordance with one aspect of the present application, a pressing and tearing method for peeling rate tests is also provided, which comprises the following steps:

S1, inputting a preset pressing force value and a preset tearing force value by an input unit, and sending the preset pressing force value and the preset tearing force value to a controller;

S2, detecting a pressing force between a sample and a press mechanism by a pressure sensor, and sending the detected pressing force value to the controller;

S3, using the controller to compare the preset pressing force value with the detected pressing force value, and driving a working table to move upward by a first drive assembly until the detected pressing force value is equal to the preset pressing force value;

S4, using the controller to control the press mechanism and the working table to translate and roll relative to each other by a second drive assembly, and using the press mechanism to press an adhesive tape;

S5, detecting a tearing force by a tension sensor, and sending the detected tearing force value to the controller;

S6, using the controller to compare the preset tearing force value with the detected tearing force value, and driving the working table to move downward by the first drive assembly until the detected tearing force value is equal to the preset tearing force value;

S7, using the controller to control the press mechanism and the working table to translate and roll relative to each other by the second drive mechanism, and using the press mechanism to tear off the adhesive tape.

In one embodiment, in the steps S3 and S6, the first drive mechanism serves as a table drive mechanism configured to drive the working table to move upward or downward; the table drive mechanism includes a second motor electrically connected to the controller and a screw rod; one end of the screw rod is connected to the second motor by a drive connection, and the other end of the screw rod is connected to the working table by a screw connection.

In this embodiment, in the steps S4 and S7, the second drive assembly serves as the table drive mechanism too, and is configured to drive the working table to move horizontally; wherein, the table drive mechanism further includes a first motor, a belt drive unit, and a guide block; the second motor is fixed on the guide block; and the table drive mechanism drives the working table to move horizontally when the guide block moves horizontally with the rotation of a convey belt of the belt drive unit.

In another embodiment, in the steps S4 and S7, the second drive assembly serves as a pressing drive mechanism; wherein, the pressing drive mechanism includes a motor and a drive element, and is configured to drive a first fixing member of the pressing mechanism to move horizontally, and drive a rolling member of the pressing mechanism to synchronously roll and translate relative to the working table.

When implementing the pressing and tearing apparatus and the method for peeling rate tests of the present application, the following advantageous effects can be achieved: the adhesive tapes are pressed by a preset pressing force in the pressing operation, and are tore off at a preset tearing angle by a preset tearing force in the tearing operation. Therefore, when different testers perform the same test respectively or one tester performs parallel tests on the same sample, the samples can be tested under the same conditions. In this way, the operation errors are effectively reduced, so that the repeatability and the stability of peeling rate tests are improved, the performance of the material can be reflected accurately, and the material which meets the requirements can be selected accordingly.

BRIEF DESCRIPTION OF THE DRAWINGS

The present application will be further described with reference to the accompanying drawings, in the accompanying drawings.

DETAILED DESCRIPTION

The present application will now be described in detail with reference to the accompanying drawings and embodiments, in order to make the object, the technical solution and the advantages of the present application more clearly. It should be understood that, the embodiments herein are only for illustration, not for limitation.

Figure 1:
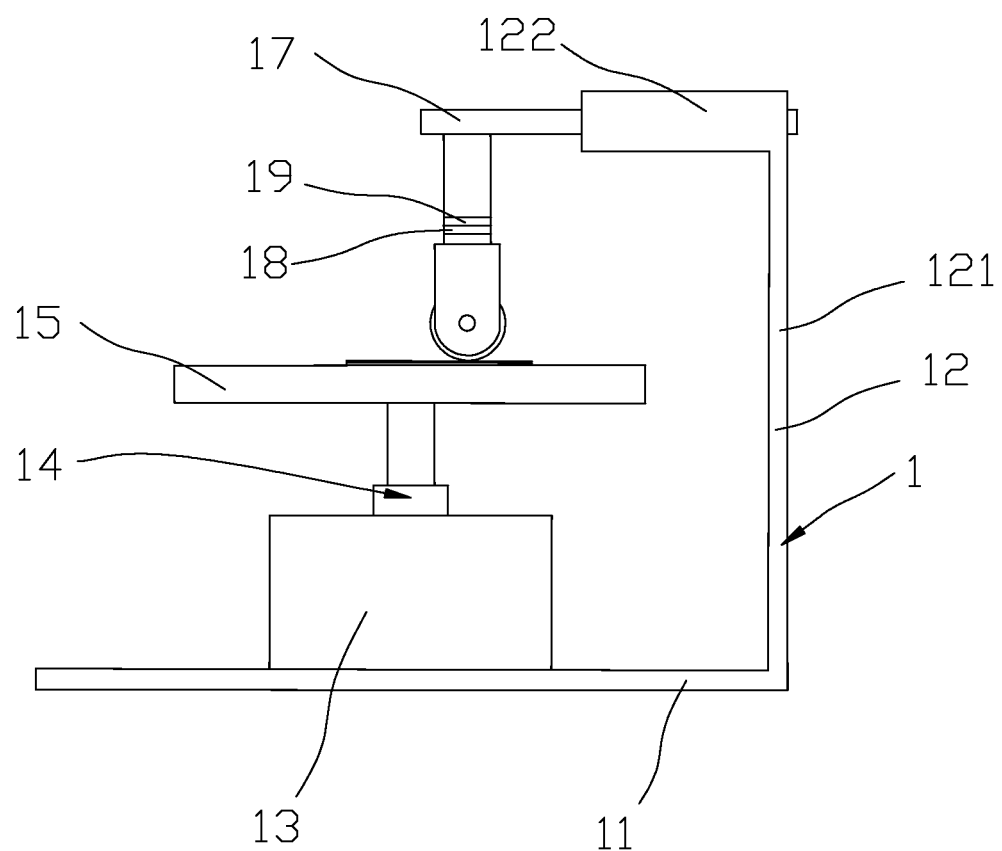
FIG. 1 is a brief structural schematic view of a pressing and tearing apparatus for peeling rate tests, according to one embodiment of the present application.
Figure 2:
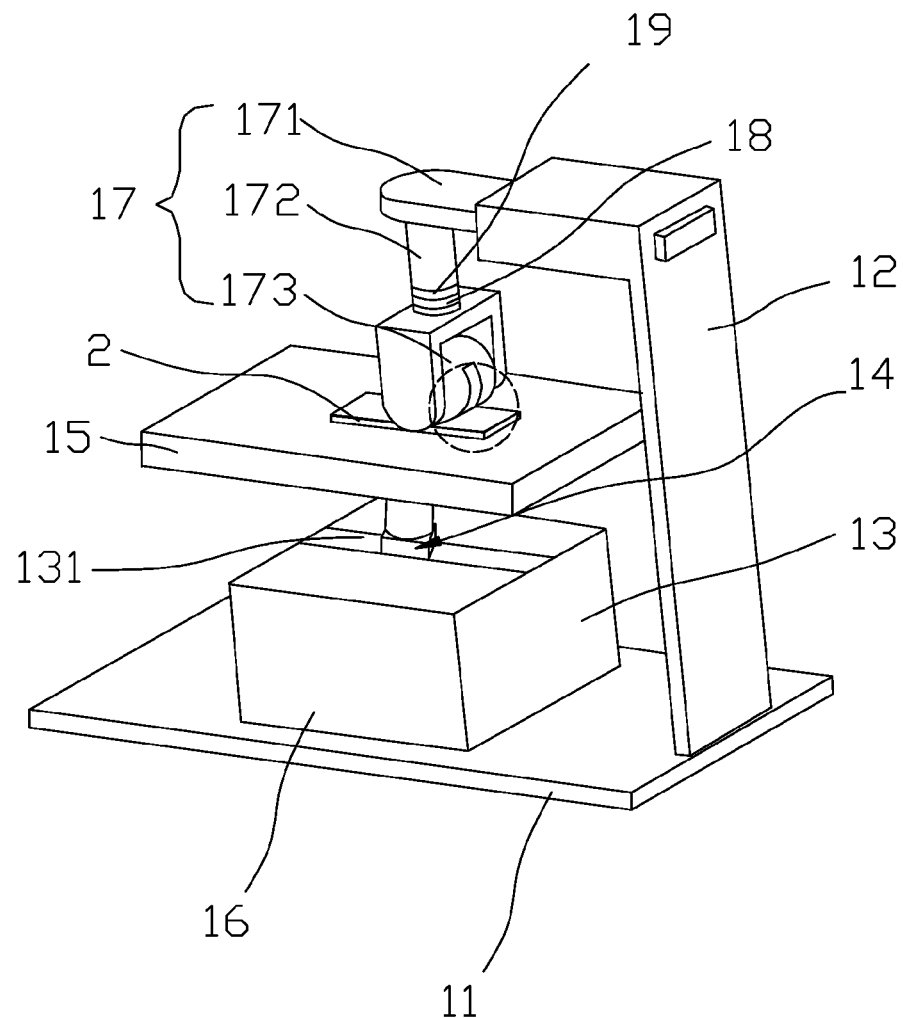
FIG. 2 is a specific structural schematic view of the pressing and tearing apparatus for peeling rate tests shown in FIG. 1.

FIGS. 1-2 show the structure of a pressing and tearing apparatus 1 for peeling rate tests according to one embodiment of the present application. Referring to FIGS. 1-2, the apparatus 1 mainly includes a base plate 11, a holding element 12, a controller 13, a table drive mechanism 14, a working table 15, an input unit 16, a press mechanism 17, a pressure sensor 18, and a tension sensor 19. Wherein the holding element 12 is fixed on the base plate 11, and is configured for holding and fixing the press mechanism 17. The controller 13 is also fixed on the base plate 11, and is configured for controlling the movement of the table drive mechanism 14 and further controlling the movement of the working table 15. The table drive mechanism 14 is disposed between the controller 13 and the working table 15; wherein, one end of the table drive mechanism 14 is electrically connected to the controller 13, and the other end of the table drive mechanism 14 is mechanically connected to the working table 15. The input unit 16 is fixed on the controller 13. The press mechanism 17 is fixed on the holding element 12, and the press mechanism 17 and the working table 15 are movable relative to each other in both the vertical direction and the horizontal direction. The pressure sensor 18 and the tension sensor 19 are fixed on the press mechanism 17. Wherein, the input unit 16, the pressure sensor 18, and the tension sensor 19 are electrically connected to the controller 13 respectively; and the controller 13 is further electrically connected to a power source (not shown).

As show in FIG. 2 specifically, the holding element 12 is fixed on the base plate 11 and configured for holding the press mechanism 17. As shown in FIG. 2, the holding element 12 is substantially L-shaped and includes a first plate 121 and a second plate 122 which are perpendicular to each other. The first plate 121 is perpendicularly fixed on the base plate 11, and the second plate 122 is fixedly connected to one end of the first plate 121 and is parallel to the base plate 11. A mounting slot (not labeled) for mounting a first fixing member 171 of the press mechanism 17 is defined in the second plate 122.

The controller 13 is fixed on the base plate 11, and is electrically connected to the input unit 16, the pressure sensor 18, and the tension sensor 19 respectively. The controller 13 is configured to receive information sent from the input unit 16, the pressure sensor 18, and the tension sensor 19 respectively, compare a preset pressing force value or a preset tearing force value received from the input unit 16 with a pressing force value detected by the pressure sensor 18 or a pressing force value detected by the tension sensor 19, and control the movement of the table drive mechanism 14. In this way, the working table 15 is controlled to move up and down vertically for adjusting the pressing force or the tearing force, and is also controlled to move leftward and rightward horizontally for finishing pressing operations and tearing operations of adhesive tapes. Furthermore, the controller 13 is connected to the power source. A guide slot 131 is defined in a side of the top of the controller 13 which is near the working table 15, according to one embodiment of the present application.

Figure 3:
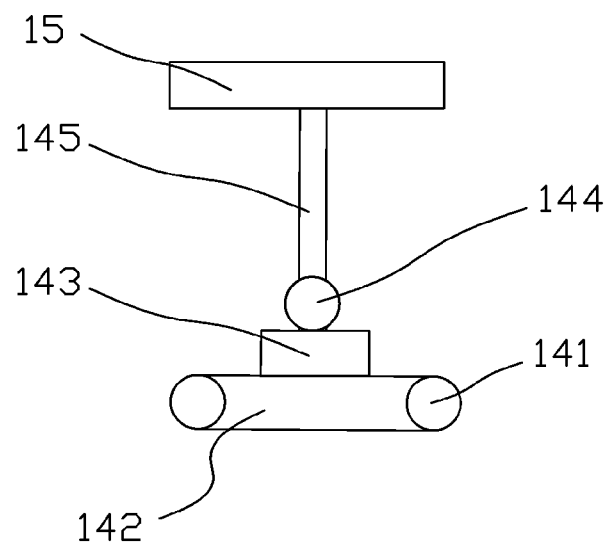
FIG. 3 is a structural schematic view of a table drive mechanism shown in FIG. 2.

Also referring to FIGS. 2 and 3, the table drive mechanism 14 includes a first motor 141, a belt drive unit 141, a guide block 143, a second motor 144, and a screw rod 145. Wherein, both the first motor 141 and the belt drive unit 142 are fixed inside the controller 13 and disposed below the guide slot 131 in the vertical direction. The first motor 141 is electrically connected to the controller 13. The guide block 143 is disposed on a convey belt (not labeled) of the belt drive unit 142, and is limited in the guide slot 131 on the top of the controller 13. The guide block 143 can move along the horizontal direction in the guide slot 131 with clockwise or anticlockwise rotation of the convey belt.

The first motor 141 is connected to a convey wheel (not labeled) of the belt drive unit 142 by a drive connection. When the first motor 141 is rotated forward, the convey belt of the belt drive unit 142 is driven to rotate clockwise by the first motor 141, and the guide block 141 fixed on the convey belt is driven to move horizontally from the left to the right in the guide slot 131. While the first motor 141 is rotated backward, the convey belt is driven to rotate anticlockwise, and the guide block 143 is driven to move horizontally from the right to the left in the guide slot 131.

Furthermore, as shown in FIG. 3, the second motor 144 is fixed on the guide block 143 and electrically connected to the controller 13. One end of the screw rod 145 is connected to the second motor 144 by a drive connection, and the other end of the screw rod 145 is connected to the working table 15 by a screw connection. Under the control of the controller 13, when the second motor 144 is rotated forward, the screw rod 145 is driven to move upward along the vertical direction, and the working table 15 is thereby driven to move upward along the vertical direction. While the second motor 144 is rotated backward, the screw rod 145 is driven to move downward along the vertical direction, and the working table 15 is thereby driven to move downward along the vertical direction. Wherein, the screw rod 145 is used to achieve a precise position of the working table 15, and thus the control precisions of the pressing force and the tearing force are improved.

As shown in FIG. 2, the working table 15 is configured to place a measured sample 2 and finish a pressing operation and a tearing operation for an adhesive tape in a peeling rate test of the measured sample 2. In this embodiment, the working table 15 is connected to the screw rod 145 of the table drive mechanism 14 by a screw connection, and is movable along the vertical direction or the horizontal direction under the drive of the table drive mechanism 14.

The input unit 16 is fixed on one side of the controller 13, and is electrically connected to the controller 13. The input unit 16 provides an operation interface for a tester, so that the tester can input the preset pressing force value and the preset tearing force value and send the values to the controller 13 via the input unit 16. Furthermore, the detected pressing force value and the detected tearing force value can be displayed by the input unit 16. In this embodiment, the input unit 16 is preferably an operation screen. Preferably, the velocity of the horizontal movement of the working table 15 can also be set by the input unit 16, and a relative horizontal movement and a relative rolling movement between the working table 15 and the press mechanism 17 can be controlled.

Figure 4:
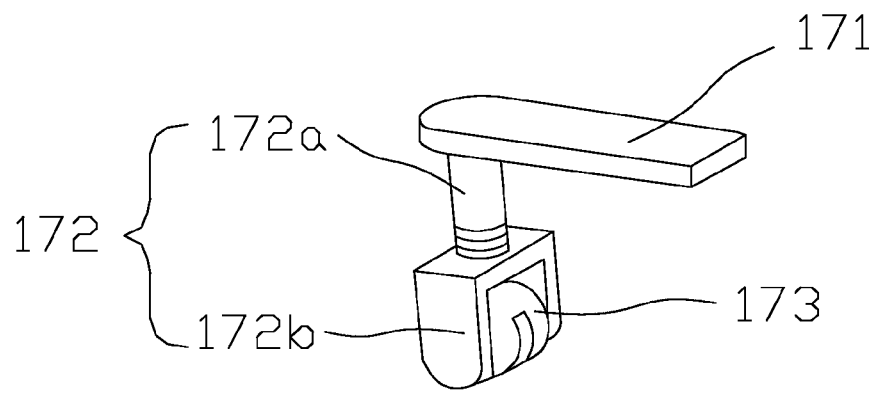
FIG. 4 is a structural schematic view of a press mechanism shown in FIG. 2.
Figure 5:
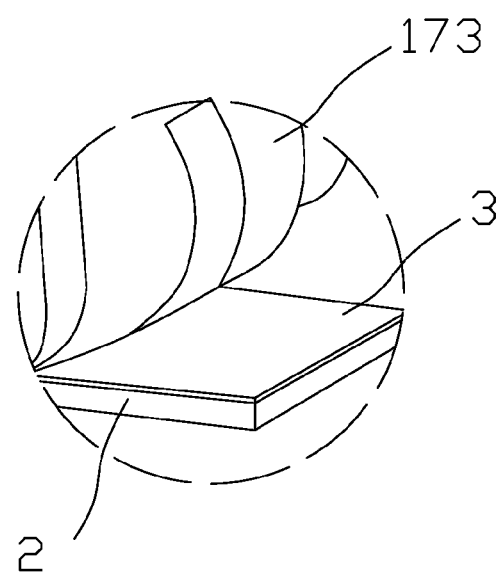
FIG. 5 is a partially enlarged view of FIG. 2.

Also referring to FIG. 2 and FIGS. 4-5, in this embodiment, the press mechanism 17 is fixed on the holding element 12, and is configured to press an adhesive tape 3 lain on the sample 2 with the preset pressing force value and tear off the adhesive tape 3 with the preset tearing force value. The press mechanism 17 is capable of synchronously rolling and translating relative to the working table 15. In this embodiment, the press mechanism 17 includes a first fixing member 171, a second fixing member 172, and a rolling member 173. The first fixing member 171 is horizontally fixed in the mounting slot of the second plate 122 of the holding element 12, and is configured for holding the whole press mechanism 17 on the holding element 12. One end of the second fixing member 172 is fixedly connected to the first fixing member 171, and the rolling member 173 is rotatably mounted in the second fixing member 172.

As shown in FIG. 4 specifically, the second fixing member 172 includes a connection portion 172a which is connected to the first fixing member 171, and a mounting portion 172b configured for rotatably mounting the rolling member 173. One end of the connection portion 172a is fixedly connected to the first fixing member 171, and the other end of the connection portion 172a extends downward and away from the first fixing member 171 (wherein, the other end of the connection portion 172a may be inclined to the first fixing member 171 or perpendicular to the first fixing member 171). The mounting portion 172b includes two mounting plates (not labeled) disposed opposite to each other. One end of one of the mounting plates is connected to one end of the other of the mounting plates by a connection plate (not labeled), and the connection plate is further fixedly connected to the connection portion 172a. Besides, a spindle (not shown) is disposed between surfaces of the two mounting plates which are opposite to each other. The rolling member 173 is disposed between the two mounting plates and is rotatable relative to the spindle.

Preferably, the rolling member 173 is a rolling wheel. In the operation of pressing the adhesive tape 3 in a peeling rate test, when the working table 15 moves relative to the press mechanism 17 in the horizontal direction, the rolling wheel may synchronously roll and translate relative to the adhesive tape 3, so that different parts of the adhesive tape 3 can be pressed onto the surface of the sample 2 by an uniform pressing force.

Besides, the pressing and tearing apparatus for peeling rate tests of the present application further includes the pressure sensor 18 and the tension sensor 19 which are fixed on the press mechanism 17. Referring to FIG. 2, the pressure sensor 18 and the tension sensor 19 are respectively fixed on the second fixing member 172 of the press mechanism 17, and are electrically connected to the controller 13 respectively. In a peeling rate test, during a pressing operation for an adhesive tape, the pressure sensor 18 detects a value of a pressing force between the rolling member 173 and the sample 2 in real time, and sends the detected value of the pressing force to the controller 13. During a tearing operation of the adhesive tape, the tension sensor 19 is used to detect a value of a tearing force between the rolling member 173 and the sample 2 in real time, and send the detected value of the tearing force to the controller 13.

Figure 6:
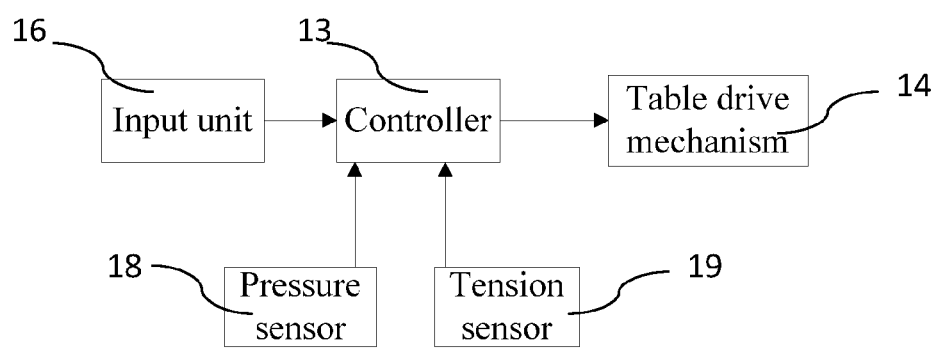
FIG. 6 is a block diagram that illustrates the working principle of the pressing and tearing apparatus for peeling rate tests shown in FIG. 1.

The working principle of the pressing and tearing apparatus for peeling rate tests shown in FIG. 1 is briefly introduced accompanying with FIG. 6.

Pretreatment: A sample 2 which has a coating layer attached thereon is pretreated by means of a Cross-Cut Test. Afterwards, the sample 2 is disposed on the working table 15, and a surface of the sample 2 to be tested is positioned upward. The coating layer may be a photoresist coating layer, a color resist coating layer, a photosensitive coating layer, or an OC (Optical clear) coating layer. Thus, an adhesive tape 3 is laid onto the surface to be tested, and no pressure is applied to the adhesive tape 3.

Pressing operation for the adhesive tape: a tester inputs a preset pressing force value using the input unit 16, and this preset pressing force value is sent to the controller 13. At the same time, a pressing force between the press mechanism 17 and the sample 2 is detected by the pressure sensor 18, and then the detected pressing force value is sent to the controller 13. The controller 13 compares the detected pressing force value with the preset pressing force value, and controls the table drive mechanism 14 to drive the working table 15 to move upward until the real-time detected pressing force value received from the pressure sensor 18 is equal to the preset pressing force value. Afterwards, the controller 13 controls the table drive mechanism 14 to drive the working table 15 to move horizontally, which makes the working table 15 move horizontally and roll synchronously relative to the press mechanism 17, and thus all parts of the adhesive tape 3 are pressed by the rolling member 173 of the press mechanism 17 with an uniform pressing force.

Tearing operation for the adhesive tape: an adhesive element (not labeled) is adhered to the surface of the rolling member 173, and a cohesive surface of the adhesive element is positioned to face the sample 2. In this embodiment, the adhesive element may be another adhesive tape.

Afterwards, the tester inputs a preset tearing force value and a preset tearing angle by the input unit 16, and the preset tearing parameters are sent to the controller 13. At the same time, the tension sensor 19 detects a value of a tearing force between the press mechanism 17 and the sample 2 and sends the detected tearing force value to the controller 13. The controller 13 compares the detected tearing force value with the preset tearing force value, and controls the table drive mechanism 14 to drive the working table 15 to move downward until the real-time detected tearing force value received from the tension sensor 19 is equal to the preset tearing force value. Afterwards, the controller 13 controls the table drive mechanism 14 to drive the working table 15 to move horizontally, which makes the working table 15 move horizontally and roll synchronously relative to the press mechanism 17, and thus the adhesive tape 3 is torn off by the rolling member 173 with the adhesive element.

Figure 7:
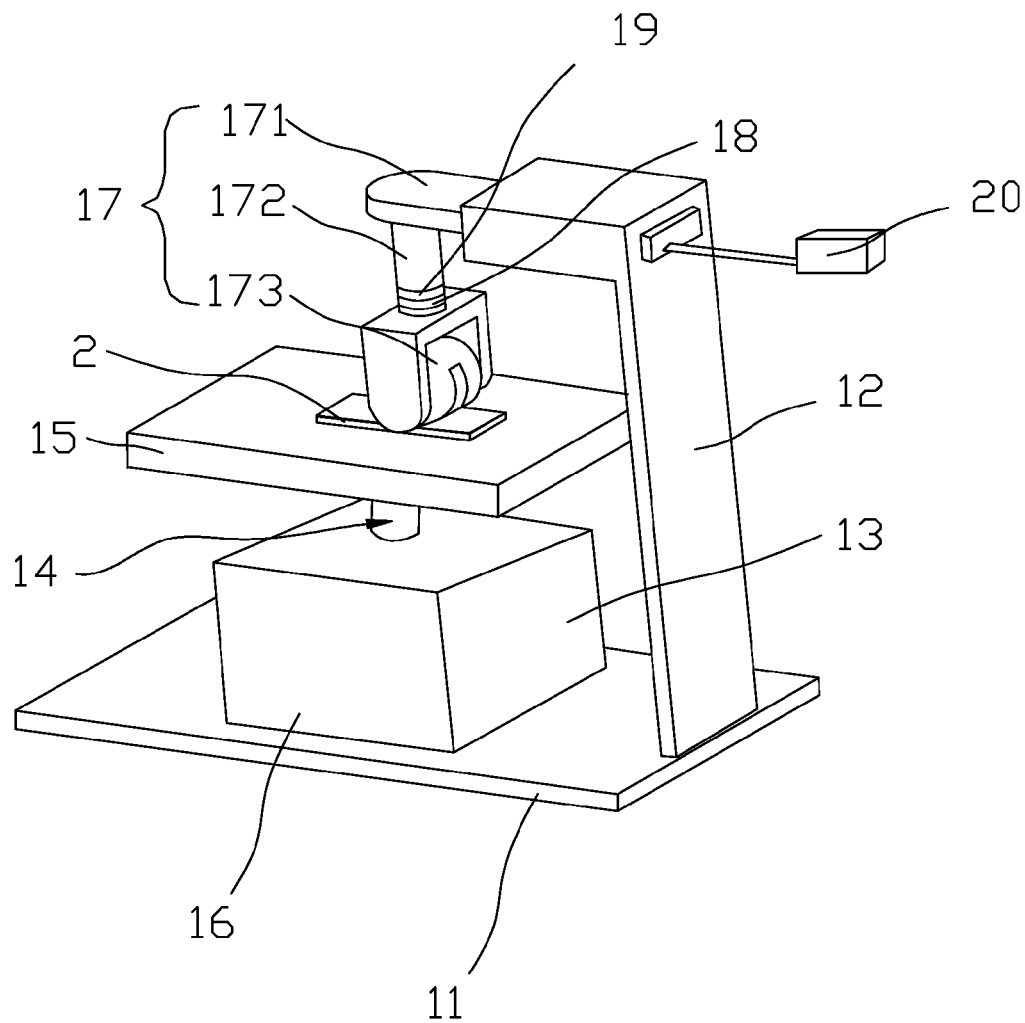
FIG. 7 is a brief structural schematic view of a pressing and tearing apparatus for peeling rate tests, according to another embodiment of the present application.

FIG. 7 is a brief structural schematic view of a pressing and tearing apparatus for peeling rate tests according to another embodiment of the present application. Referring to FIG. 7, in another embodiment of the present application, a pressing and tearing apparatus 1 for peeling rate tests mainly includes a base plate 11, a holding element 12, a controller 13, a table drive mechanism 14, a working table 15, an input unit 16, a press mechanism 17, a pressure sensor 18, and a tension sensor 19. In this embodiment, the structures, functions, and connections of all the components except the table drive mechanism 14 and the press mechanism 17 are similar to the corresponding components of the embodiment shown in FIG. 1, and therefore do not need to be repeated here. In additional, in this embodiment, the pressing and tearing apparatus 1 for peeling rate tests further includes a pressing drive mechanism 20.

In the present application, relative movements along the vertical direction between the press mechanism 17 and the working table 15 are achieved by the table drive mechanism 14, and relative synchronous translations and rotations along the horizontal direction between the press mechanism 17 and the working table 15 are achieved by the pressing drive mechanism 20. Specifically, the table drive mechanism 14 drives the working table 15 to move upward and downward in the vertical direction; and the pressing drive mechanism 20 drives the press mechanism 17 to move in the horizontal direction and roll synchronously at the same time.

In this embodiment, no guide slot 131 is defined in the controller 13. The table drive mechanism 14 only includes a motor (not shown) fixed within the controller 13 and a screw rod 145. Wherein, the motor is electrically connected to the controller 13; one end of the screw rod 145 is connected to the motor by a drive connection, and the other end of the screw rod 145 is connected to the working table 15 by a screw connection. Therefore, the working table 15 can only move upward and downward in the vertical direction under the drive of the table drive mechanism 14, and cannot move leftward and rightward along the horizontal direction.

At this time, under the control of the controller 13, when the motor is rotated forward, the screw rod 145 is driven to move upward along the vertical direction, and the working table 15 is thereby driven to move upward along the vertical direction. While the motor is rotated backward, the screw rod 145 is driven to move downward along the vertical direction, and the working table 15 is thereby driven to move downward along the vertical direction. In this embodiment, the screw rod 145 is used to achieve a precise position of the working table 15, and thus the control precisions of the pressing force and the tearing force are improved.

The press mechanism 17 includes a first fixing member 171, a second fixing member 172, and a rolling member 173. The structures of these components can refer to the embodiment shown in FIG. 1. Differing from the corresponding components of the embodiment shown in FIG. 1, the first fixing member 171 is mounted in the mounting slot of the second plate 122 and can move in the mounting slot.

The pressing drive mechanism 20 includes a motor (not shown) and a drive element (not shown) which is connected to the first fixing member 173 of the press mechanism 17 by a drive connection. The motor is disposed inside the controller 13, and is electrically connected to the controller 13. The drive element can be positioned inside the holding element 12, and can also be positioned outside the holding element 12. Wherein, one side of the drive element is connected to the motor by a drive connection, and the other side of the drive element is fixedly connected to the first fixing member 171. Drive mechanism well known to those skilled in the art can be used as the drive element in this embodiment, and does not need to be detailed here.

Under the control of the controller 13, when the motor of the pressing drive mechanism 20 is rotated forward, the drive element is driven to move rightward along the horizontal direction, and the press mechanism 17 is thereby driven to synchronously move rightward along the horizontal direction and roll relative to the working table 15. While the motor of the pressing drive mechanism 20 is rotated backward, the drive element is driven to move leftward along the horizontal direction, and the press mechanism 17 is thereby driven to synchronously move leftward along the vertical direction and roll relative to the working table 15.

In other embodiments of the present application, the first fixing member 171 is substantially tabular and projects out of both two ends of the mounting slot of the second plate 122. One end of the first fixing member 171 which is near the first plate 121 forms a moving part (not labeled) configured to drive the first fixing member 171 to move inside the mounting slot. The tester can press or move the moving part manually, and thus the first fixing member 171 can be moved leftward and rightward along the horizontal direction in the mounting slot of the second plate 122.

Figure 8:
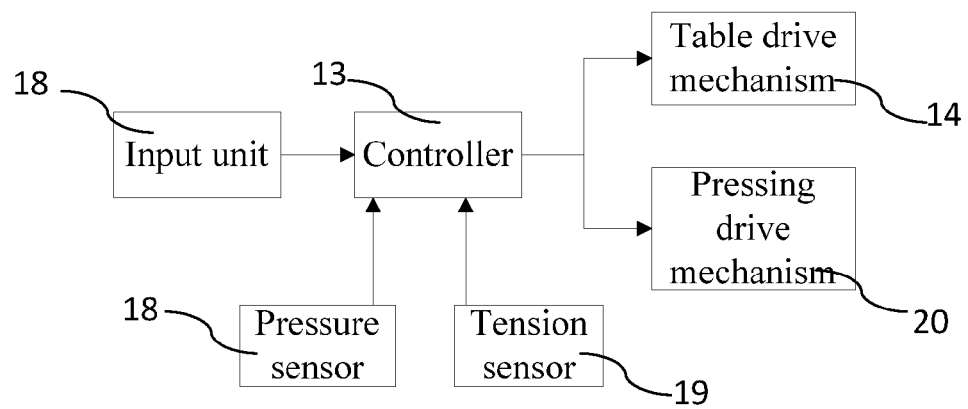
FIG. 8 is a block diagram that illustrates the working principle of the pressing and tearing apparatus for peeling rate tests shown in FIG. 7.

The working principle of the pressing and tearing apparatus for peeling rate tests shown in FIG. 7 is briefly introduced accompanying with FIG. 8.

Pretreatment: the process of the pretreatment is the same as that of the embodiment shown in FIG. 1, and does not need to be repeated here.

Pressing operation for the adhesive tape: The controller 13 controls the pressing drive mechanism 20 to drive the press mechanism 17 to move in the horizontal direction, so that the press mechanism 17 is capable of synchronously moving in the horizontal direction and rolling, and all parts of the adhesive tape 3 are pressed with an uniform pressing force or torn off with an uniform tearing force by the rolling member 173 of the press mechanism 17.

Figure 9:
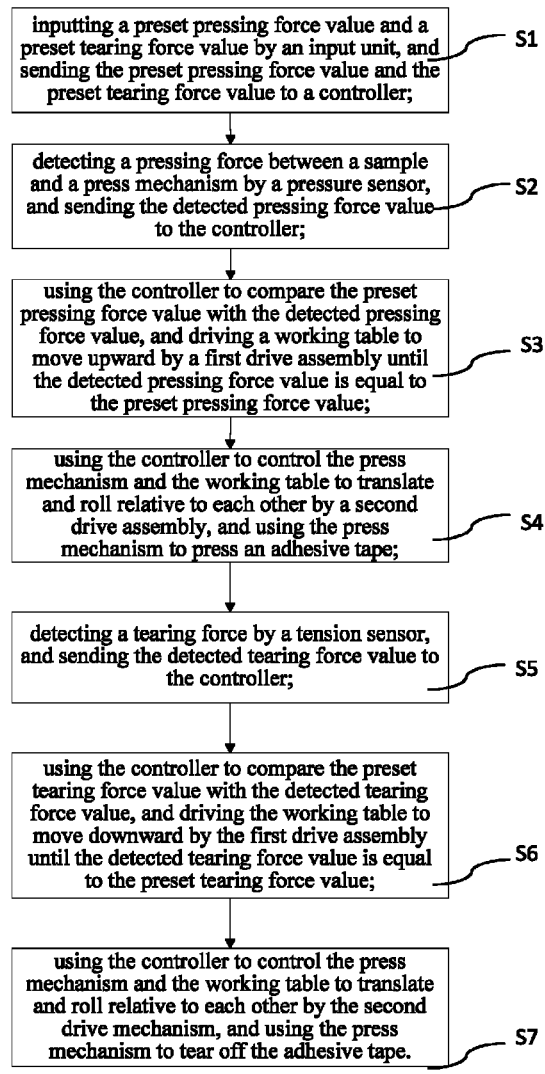
FIG. 9 is a flow chart of a pressing and tearing method for peeling rate tests, according to the present application.

As shown in FIG. 9, the present application further provides a pressing and tearing method for peeling rate tests, which is achieved by the aforementioned pressing and tearing apparatus 1. The method comprises the following steps:

S1, inputting a preset pressing force value and a preset tearing force value by the input unit 16, and sending the preset pressing force value and the preset tearing force value to the controller 13; S2, detecting a pressing force between the sample 2 and the press mechanism 17 by the pressure sensor 18, and sending the detected pressing force value to the controller 13;

S3, using the controller 13 to compare the preset pressing force value with the detected pressing force value, and driving the working table 15 to move upward by the first drive assembly until the detected pressing force value is equal to the preset pressing force value;

S4, using the controller 13 to control the press mechanism 17 and the working table 15 to translate and roll relative to each other by a second drive assembly, and using the press mechanism 17 to press an adhesive tape;

S5, detecting a tearing force by the tension sensor 19, and sending the detected tearing force value to the controller 13;

S6, using the controller 13 to compare the preset tearing force value with the detected tearing force value, and driving the working table 15 to move downward by the first drive assembly until the detected tearing force value is equal to the preset tearing force value;

S7, using the controller 13 to control the press mechanism 17 and the working table 15 to translate and roll relative to each other by the second drive mechanism, and using the press mechanism to tear off the adhesive tape.

In the embodiment shown in FIG. 1, both the first drive assembly and the second drive assembly refer to the table drive mechanism 14. In this way, the working table 15 is enabled to move along both the horizontal direction and the vertical direction, and the press mechanism 17 is fixed.

While in the embodiment shown in FIG. 7, the first drive assembly refers to the table drive mechanism 14, and the second drive assembly refers to the pressing drive mechanism 20. Specifically, the first drive mechanism is configured to drive the working table 15 to move upward and downward; while the second drive mechanism is configured to drive the press mechanism 17 to move in the horizontal direction. In this embodiment, the working table 15 can only move in the vertical direction.

After the pressing operation and the tearing operation are completed, when carrying out peeling rate tests, the peeling rates can be calculated by comparing the areas of the same portion of the coating layer of the sample 2 before and after the operations. The calculating method can be a conventional calculating method. In order to see the peeling situation of the coating layer on the surface of the sample 2 more clearly, preferably, the sample 2 is observed using an optical microscope, and the areas of the same portion of the coating layer of the sample 2 before and after the operations are compared with each other.

By using the pressing and tearing apparatus and method for peeling rate tests according to the present application, the adhesive tapes are pressed by a preset pressing force in the pressing operation, and are torn off at a preset tearing angle by a preset tearing force in the tearing operation. Therefore, when different testers perform the same test respectively or one tester performs parallel tests on the same sample, the samples can be tested under the same conditions. In this way, the operation errors are effectively reduced, so that the repeatability and the stability of peeling rate tests are improved, the performance of the material can be reflected accurately, and the material which meets the requirements can be selected accordingly.

Therefore, the pressing and tearing apparatus and method for peeling rate tests according to the present application can be widely used in experiments in which the products are coating with coating layers and for which peeling rate tests need to be carried out. The experiments for example include peeling rate tests for the photoresist, the PS (Polystyrene), the OC (Optically Clear) adhesive or the PC (Polycarbonate) in the TFT-LCD industry, as well as the adhesion test of the coating. The present application can also be used in the experiments in which pressing forces need to be tested.

Those mentioned above are the detailed descriptions of the embodiments accompanying the drawings. However, the present application is not limited to the embodiments above. In the inspiration of the present application, one skilled in the art can also make many modifications without breaking away from the subject of the present application and the protection scope of the claims. All these modifications belong to the protection of the present application.

The invention claimed is:

1. A pressing and tearing apparatus for peeling rate tests, comprising:
    a working table configured to place a sample;
    a press mechanism disposed above the working table, and being capable of synchronously rolling and translating relative to the working table;
    an input unit configured for inputting a preset pressing force value and a preset tearing force value;
    a pressure sensor configured for detecting a pressing force between the sample and the press mechanism;
    a tension sensor configured for detecting a tearing force between the sample and the press mechanism;
    a controller electrically connected to the input unit, the pressure sensor, and the tension sensor respectively; wherein, the controller is configured to compare the detected pressing force value received from the pressure sensor or the detected tearing force value received from the tension sensor with the preset pressing force value and the preset tearing force value received from the input unit, and drive the working table to move upward or downward for adjusting the pressing forces or the tearing forces; the controller is further configured to drive the press mechanism to roll and translate synchronously relative to the working table for pressing or tearing off adhesive tapes; and
    a drive assembly configured to drive the working table to move upward or downward and drive the press mechanism to roll and translate synchronously relative to the working table under the control of the controller;
    wherein, the drive assembly includes a table drive mechanism; a guide slot is defined in the controller; the table drive mechanism includes a first motor, a belt drive unit, and a guide block; wherein, the first motor is electrically connected to the controller; the belt drive unit is connected to the first motor by a drive connection; the guide block is disposed on the belt drive unit and is limited in the guide slot; the guide block is movable in the guide slot with the rotation of a convey belt of the belt drive unit.

2. The pressing and tearing apparatus for peeling rate tests according to claim 1, wherein, the apparatus further includes a base plate and a holding element; the controller and the holding element are fixed on the base plate, and a mounting slot configured for mounting a first fixing member of the press mechanism is defined in the holding element.

3. The pressing and tearing apparatus for peeling rate tests according to claim 2, wherein, the press mechanism further includes a second fixing member and a rolling member configured to press and tear off the adhesive tapes; one end of the second fixing member is fixedly connected to the first fixing member, and the rolling member is rotatably mounted on the second fixing member.

4. The pressing and tearing apparatus for peeling rate tests according to claim 3, wherein, the second fixing member includes a mounting portion configured for rotatably mounting the rolling member;
the mounting portion includes two mounting plates disposed opposite to each other; one end of one of the mounting plates is connected to one end of the other of the mounting plates by a connection plate; a spindle is disposed between surfaces of the two mounting plates that are opposite to each other; the rolling member is disposed between the two mounting plates and is rotatable relative to the spindle.

5. The pressing and tearing apparatus for peeling rate tests according to claim 4, wherein, the second fixing member further includes a connection portion; one end of the connection portion is fixedly connected to the first fixing member, and the other end of the connection portion is fixedly connected to the connection plate of the mounting portion.

6. The pressing and tearing apparatus for peeling rate tests according to claim 3, wherein, two ends of the first fixing member project from the mounting slot; and one end of the first fixing member forms a moving part configured to drive the first fixing member to move inside the mounting slot.

7. The pressing and tearing apparatus for peeling rate tests according to claim 3, the table drive mechanism further includes a second motor and a screw rod; wherein, the second motor is electrically connected to the controller; one end of the screw rod is connected to the second motor by a drive connection, and the other end of the screw rod is connected to the working table by a screw connection.

8. The pressing and tearing apparatus for peeling rate tests according to claim 7, wherein,
    the second motor is fixed on the guide block.

9. The pressing and tearing apparatus for peeling rate tests according to claim 7, wherein, the drive assembly includes a pressing drive mechanism, and the pressing drive mechanism includes a motor electrically connected to the controller and a drive element configured to drive the press mechanism to roll and translate synchronously relative to the working table.

10. The pressing and tearing apparatus for peeling rate tests according to claim 9, wherein, the first fixing member of the press mechanism is movable in the mounting slot of the holding element.

11. A pressing and tearing method for peeling rate tests, comprising the following steps:
    S1, inputting a preset pressing force value and a preset tearing force value by an input unit, and sending the preset pressing force value and the preset tearing force value to a controller;
    S2, detecting a pressing force between a sample and a press mechanism by a pressure sensor, and sending the detected pressing force value to the controller;
    S3, using the controller to compare the preset pressing force value with the detected pressing force value, and driving a working table to move upward by a first drive assembly until the detected pressing force value is equal to the preset pressing force value;
    S4, using the controller to control the press mechanism and the working table to translate and roll relative to each other by a second drive assembly, and using the press mechanism to press an adhesive tape;
    S5, detecting a tearing force by a tension sensor, and sending the detected tearing force value to the controller;
    S6, using the controller to compare the preset tearing force value with the detected tearing force value, and driving the working table to move downward by the first drive assembly until the detected tearing force value is equal to the preset tearing force value;

S7, using the controller to control the press mechanism and the working table to translate and roll relative to each other by the second drive mechanism, and using the press mechanism to tear off the adhesive tape;

wherein, in the steps S4 and S7, the second drive assembly serves as a table drive mechanism configured to drive the working table to move horizontally; wherein, the table drive mechanism includes a first motor, a belt drive unit, and a guide block; the table drive mechanism drives the working table to move horizontally when the guide block moves horizontally with the rotation of a convey belt of the belt drive unit.

12. The pressing and tearing method for peeling rate tests according to claim 11, wherein, in the steps S3 and S6, the first drive assembly serves as the table drive mechanism too, and is configured to drive the working table to move upward or downward; the table drive mechanism further includes a second motor electrically connected to the controller and a screw rod; one end of the screw rod is connected to the second motor by a drive connection, and the other end of the screw rod is connected to the working table by a screw connection.

13. The pressing and tearing method for peeling rate tests according to claim 12, wherein, the second motor is fixed on the guide block.

14. The pressing and tearing method for peeling rate tests according to claim 12, wherein, in the steps S4 and S7, the second drive assembly serves as a pressing drive mechanism; wherein, the pressing drive mechanism includes a motor and a drive element, and is configured to drive a first fixing member of the pressing mechanism to move horizontally, and drive a rolling member of the pressing mechanism to synchronously roll and translate relative to the working table.

* * * * *